12/25/84    OR    4,489,730

United States Patent [19]
Jingu

[11] Patent Number: 4,489,730
[45] Date of Patent: Dec. 25, 1984

[54] ULTRASONIC TRANSDUCER PROBE

[75] Inventor: Masaharu Jingu, Otawara, Japan

[73] Assignee: Tokyo Shibaura Denki Kabushiki Kaisha, Japan

[21] Appl. No.: 511,285

[22] Filed: Jul. 6, 1983

[30] Foreign Application Priority Data

Jul. 8, 1982 [JP] Japan .................. 57-104087

[51] Int. Cl.³ .............................. A61B 10/00
[52] U.S. Cl. .................. 128/660; 128/24 A
[58] Field of Search .............. 128/660, 661, 24 A

[56] References Cited

U.S. PATENT DOCUMENTS

| | | |
|---|---|---|
| 4,029,084 | 6/1977 | Soldner . |
| 4,108,165 | 8/1978 | Kopp et al. . |
| 4,289,139 | 9/1981 | Enjoji et al. . |
| 4,387,721 | 6/1983 | Enjoji .................. 128/660 |
| 4,402,324 | 9/1983 | Lindgren et al. ........... 128/660 |
| 4,408,611 | 10/1983 | Enjoji . |

Primary Examiner—Kyle L. Howell
Assistant Examiner—Francis J. Jaworski
Attorney, Agent, or Firm—Finnegan, Henderson, Farabow, Garrett & Dunner

[57] ABSTRACT

An ultrasonic transducer probe for connection to ultrasonic diagnostic imaging apparatus for guiding a cannula into proper position for insertion into an objective region of the body of a patient under examination comprises a block-like carrier whose application surface is to be brought into contact with the body the carrier having a plurality of transducer elements equidistantly arranged in at least in one row across the application surface of the carrier, and having a wedge-shaped cavity extending laterally across the carrier diverging from a slot dividing the row of transducer elements into the surface opposite the application surface, and a cannula guide adapter dimensioned to fit within the cavity of the carrier detachably, the adapter being selectably reversible in the cavity and having channels in the lateral sides aligned with the slot for forming cannula guide paths radiating outward therefrom when the adapter is fitted into the cavity.

11 Claims, 8 Drawing Figures

ULTRASONIC TRANSDUCER PROBE

BACKGROUND OF THE INVENTION

This invention relates to an ultrasonic transducer probe which may be used in inserting a cannula through a region of the body of a patient to be diagnosed, e.g., in a biopsy.

In the biopsy, tissues or body fluids may be extracted from the kidney, liver and other internal body organs by means of a suitable cannula for diagnostic purposes. Also, in X-ray angiography, a cannula with an injector is pierced into blood vessels and the like for injecting a contrast medium in examination for morbid changes in a brain, heart, abdominal organs, etc. Moreover, fluids may be extracted from a body. For example, amniotic fluids may be extracted from the uterus of a pregnant woman for diagnostic purposes, or blood or medication may be injected into a fetal body.

In all these cases, it is very important to prevent undue damage to essential organs or wrong extraction of tissues in the use of the probe.

Such apparatus is described, for example, in U.S. Pat. No. 4,108,165 issued Aug. 22, 1978, to Edward L. Kopp et al. under the title "Transducer Probe for Pulse-Echo Ultrasonic Exploration." In this patent is taught ultrasonic diagnostic transducer apparatus and a combination of such apparatus and a cannula guide means, whereby an ultrasonic beam is transmitted into the body of a patient to be examined, and a sectional image of the interior of the body is obtained by reproducing the ultrasonic-echo pulses of the beam on a picture screen. The cannula is inserted into the body while the positional relation between the cannula and the internal region to be examined, as well as the state of the cannula, is reflected on the picture screen.

Apparatus is also known in which a carrier, having ultrasonic transducer elements arranged thereon, includes a tapered cannula guide slot, whereby the movement of the cannula may be observed by watching a sectional image plane in the body of a patient while the ultrasonic transducer elements are driven successively, the direction of the cannula being optionally selected within a fixed range. This apparatus is described in U.S. Pat. No. 4,029,084, issued on June 14, 1977, to Richard Soldner, and entitled "Ultrasonic Applicator with Guide Slot for Puncturing Cannula."

U.S. Pat. No. 4,289,139, issued on Sept. 15, 1981 to Susumu Enjoji et al., and assigned to the assignee of this invention, describes an ultrasonic transducer probe having a removable cannula guide block with a triangularly shaped lateral cross section. The block is fitted into a cavity of complementary shape in the probe and includes a cannula guide slot with a wide opening lying along the wide portion of the block and tapering toward the application surface. A narrow slot in the guide block interconnects the guide slot in the face of the block for permitting the block to be removed while the cannula is maintained in its proper position. This arrangement facilitates the taking of X-ray photographs in some cases. The removable block also simplifies the sterilization of the apparatus.

An improvement in the apparatus of U.S. Pat. No. 4,289,139 is taught in U.S. Pat. No. 238,203, filed Feb. 26, 1981, by Susumu Enjoji under the title "A Probe for Ultrasonic Imaging Apparatus," now U.S. Pat. No. 4,408,611. In this improvement, the structure of the removable guide block permits easier and more precise insertion of the block into the probe and facilitates the removal of the block from the probe.

In the above-described examples, however, relative displacement between the carrier body and the cannula is required to remove the carrier of the probe from the surface of the patient while maintaining the state and position of the inserted cannula. For this reason an operational difficulty can be present. In many cases where X-rays need to be taken, it would be very advantageous to be able to remove the entire transducer probe while maintaining the cannula in proper position.

In accordance with the foregoing, it is a general object of the present invention to improve ultrasonic transducer probes for use in inserting a cannula through a region of the body of a patient to be diagnosed, which facilitates the operation and the taking of X-rays of the area under diagnosis.

SUMMARY OF THE INVENTION

The principal object of the present invention is the provision of an improved ultrasonic transducer probe, wherein the entire probe can be easily removed from the patient's body while maintaining the state and position of the cannula already inserted into the predetermined portion of the patient.

Another object of the present invention is the provision of an improved ultrasonic transducer probe which enables a cannula to be maintained in a carrier body of the probe at a selected position within a fixed range of a tapered cannula guide slot, while the probe is removed.

These objects and other features and advantages will become readily apparent upon reference to the following description when taken in conjunction with the appended drawings.

BREIF DESCRIPTION OF THE DRAWINGS

FIG. 1b is a perspective view of the application surface of the transducer probe of FIG. 1a;

FIG. 2b is a plan view of the transducer probe shown in FIG. 2a;

FIG. 2c is a bottom view of the transducer probe shown in FIG. 2a;

DETAILED DESCRIPTION OF THE INVENTION

Figure 1A:
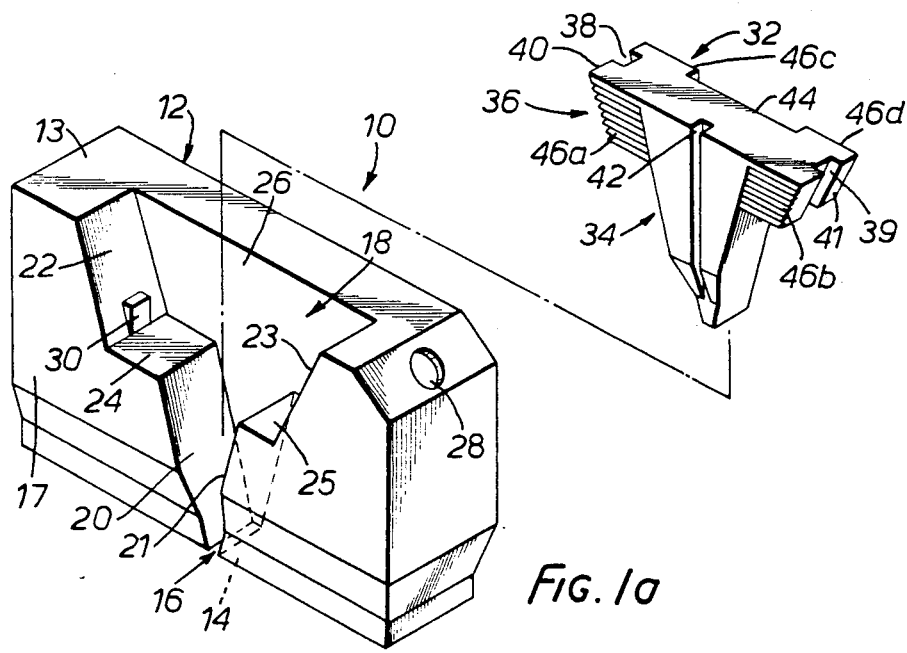
FIG. 1a is an exploded perspective view of the transducer probe construction of the present invention.
Figure 1B:
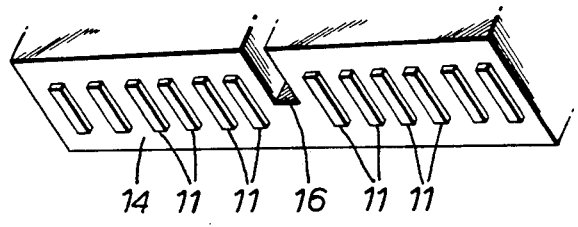

Referring now to the figures and FIGS. 1a and 1b in particular, there is shown an exploded view, transducer probe 10 comprising a block-like carrier 12 having a plurality of ultrasonic transducer elements 11 arranged in at least one row on an application surface 14 adapted to be located on the body surface of a patient. The carrier 12 includes a slot 16 extending partly across the application surface 14 between the transducer elements 11 at substantially the longitudinal center of the surface.

A wedge-shaped cavity 18 is defined by two pairs of the mutually facing offset tapered walls 20, 21, and 22, 23 opening symmetrically on both sides of an axis extending perpendicular to the application surface 14, the edges of the slot 16 defining the bottom of the cavity. Horizontal surfaces 24, 25, respectively, define the offset between the walls 20, 21 terminating in the slot 16 and the walls 22, 23 diverging upwardly into the upper surface 13 of the carrier 12. A cable bore 28 for receiving a cable (not shown) for connecting the individual transducer elements 11 to an electric transmitter-receiver section of an ultrasonic diagnostic apparatus (not shown) is formed in a convenient surface of the carrier 12.

The carrier 12 further includes a pair of projections 30 as stopper means to engage an adapter 32, the projections being formed on each of the mutually facing tapered walls 22, 23 adjoining the horizontal surfaces 24, 25.

The body of carrier 12 may be, for example, approximately 100 mm long, 60 mm high and 30 mm wide. In a carrier of such dimensions, the width of the wedge-shaped cavity 18 in the upper surface 13 of the carrier is about 70 mm and converges to the slot 16 of about 3 mm. At the horizontal surfaces 24, 25, the width of the cavity is about 50 mm between the walls 22, 23 and about 40 mm between the walls 21, 22.

The height of the projections 30 is determined to permit the adapter to be slid upwardly a short distance and then removed forwardly while the carrier is held in position by the hand of an operative grasping the area of the lateral inner wall of the carrier above the upper surface of the adapter, for reasons explained hereinafter.

The distribution of the transducer elements 11 as shown on the application surface 14 is purely exemplary. In an actual transducer, approximately 120 transducer elements are positioned on the application surface, each element having a width, for example, of about 0.6 mm, and arranged at intervals of about 0.1 mm. Where the slot 16 opens into the approximate center of the application surface the space between the adjacent elements 11 is widened.

Figure 2A:
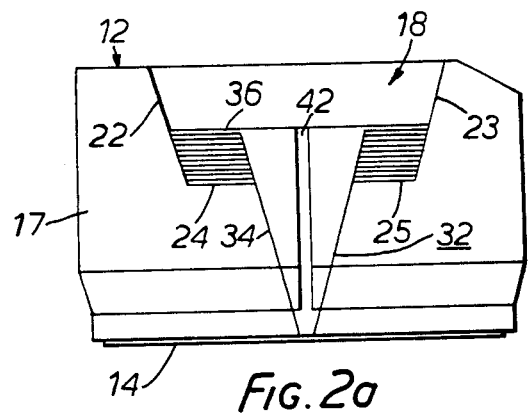
FIG. 2a is a front view of the transducer probe showing the cannula guide adapter of FIG. 1 fitted into the carrier of the probe.

The adapter 32 is substantially complementary in shape to the wedge-shaped cavity 18 in the carrier 12 so as to be fitted into the cavity and may be made of elastic synthetic resins. The height of the adapter 32, however, is somewhat less than the height of the cavity 18, the upper surface of the adapter, when inserted in the cavity, being parallel to the upper surface 13 of the carrier 12 but about half the distance between the horizontal surfaces 24, 25 and the upper surface 13, as shown in FIG. 2a.

The adapter 32 includes a cannula guide portion 34 and a carrier engaging portion 36. The cannula guide portion 34 comprises the lower portion of the adapter 32 between the opposing walls 20, 21 and the upper portion of the adapter substantially bounded by the diverging projections of the walls 20, 21 when the adapter is inserted in the carrier. The carrier engaging portion 36 includes the upper portions of the adapter 32 between the horizontal surfaces 24, 25 and the upper surface 13 extending outwardly from the projections of the walls 20, 21. A pair of grooves 38, 39 having a defined depth is cut into the two diverging surfaces 40, 41 of the engaging portion 36 complementary to the walls 22, 23 of the carrier 12 for engaging the projections 30 of the carrier.

The outer and inner vertical walls 46a–d of the carrier engaging portion 36 are grooved with horizontal ridges to facilitate handling of the adapter 32, only the grooves on the outer walls being shown.

The adapter 32 is reversible with respect to the carrier 12, i.e., the adapter may be inserted into the cavity 18 with either of the lateral walls of the adapter facing the vertical wall 26 of the cavity. Cannula guide means may then be formed on each lateral wall of the adapter for use as convenient.

As illustrated in FIG. 1a and FIG. 2a, the outer lateral wall of the adapter 32 contains a single vertical cannular guide channel 42, whereas the inner lateral wall (FIG. 1) is formed with a shallow, triangular cavity 44 extending from a wide portion in the top surface of the adapter and converging to a slot (not shown) in the bottom edge of the adapter. The channel 42 and the shallow cavity 44 each terminates in a slot (not shown) aligned with the slot 16 in the carrier.

When the adapter 32, formed as shown in FIG. 1, is inserted into the cavity 18, the cavity 44 and the wall 26 of the carrier 12 form a cannula guide path with converging side walls. The surgeon may then selectively position the the cannula in the triangular guide path at any angle within the width of the path.

Figure 3A:
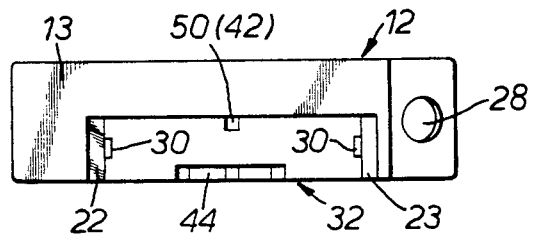
FIGS. 3a and 3b are views similar to FIGS. 2a and 2b, wherein the cannula guide adapter has been fitted in the carrier body of the transducer probe after being rotated by 180 degrees from the arrangement in FIG. 1 and the cannula guide slot has been modified.
Figure 3B:
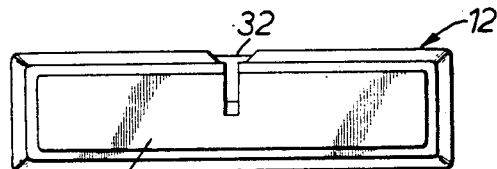

Alternatively, the adapter 32 may be reversed from the position shown in FIG. 1 and the channel 42 positioned next to the wall 26 of the carrier 12. The channel 42 is then closed by the wall 26 and a single conduit 50, as shown in FIG. 3a, is formed for guiding a cannula perpendicularly to the application surface 14.

Figure 4:
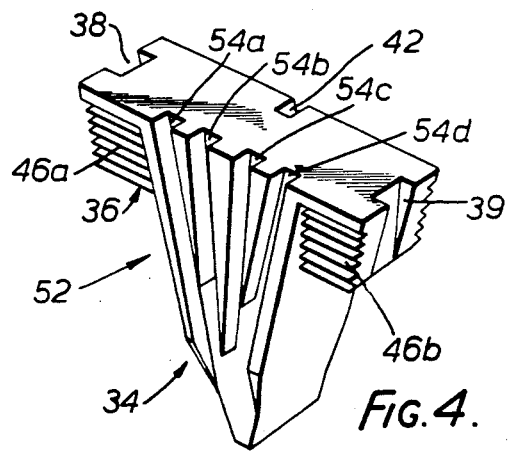
FIG. 4 is a perspective view showing a modification of the cannula guide adapter of FIG. 1.

Under the invention, a plurality of cannula guide paths may be formed on at least one lateral surface of the adapter. For example, in the embodiment of FIG. 4, a cannula guide adapter 52 is provided with a plurality of cannula guide channels 54a–d extending radially from the bottom to the top of the adapter 52 in place of the triangular space 44 shown in FIG. 1. The cannula guide adapter 52 may be fitted in the wedge-shaped cavity 18 of the carrier 12 with the channel 42 in front, whereby four guide paths are defined by the channels 54 and the inner lateral wall 26 of the cavity. Cannula guide paths at predetermined radial angles from the bottom to the top of the adapter 52 are thus provided. The puncturing cannula is advanced precisely through the selected closed path and inserted into the objective region of the body of the patient.

Figure 2B:
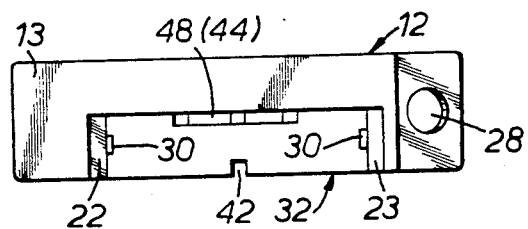
Figure 2C:
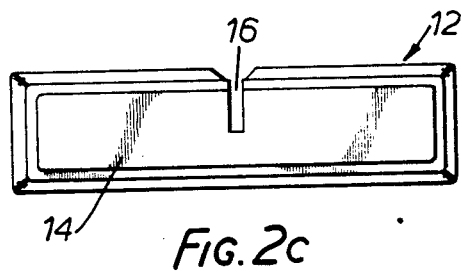

Any convenient number of cannula guide paths may be provided on the lateral surfaces of the cannula guide adapter. For example, in FIGS. 2b and 3a three guide paths are shown.

Now there will be described the operation of the above-mentioned ultrasonic transducer probe.

First, the cannula guide adapter 32 or 52, which has previously been sterilized, is fitted in the wedge-shaped cavity 18 of the carrier 12 with the channel 42, for example, being in front and the projections 30 defined on the mutually facing tapered walls 22, 23 of the carrier 12 fitted into the grooves 38, 39 cut into the side surface 40, 41 of the cannula guide adapter. The cannula guide adapter is thus securely fitted in the wedge-shaped cavity 18. The cannula guide slot path or paths are thereby defined by the channels 44, 48 or 54 of the adapter and the inner lateral wall 26 of the cavity 18.

Then the transducer probe 10 is placed on the body surface of the patient corresponding to the region which requires examination or injection of contrast medium by means of a cannula. Ultrasonic search signals are transmitted toward the interior of the patient body and echo signals are received from the search signal intercepting acoustic discontinuities. An ultrasonic sectional image of the region is displayed on a display unit of an ultrasonic diagnostic apparatus.

Thereafter, the puncturing cannula is inserted into a guide path. The displacement of the cannula is then determined from the depth and relative position of the objective region in the patient body, while the operator observes the display of the sectional image. Thereupon, the cannula is introduced at a prescribed angle and inserted into the body of the patient. At the same time, an echoic image of the cannula is also displayed on the display unit, whereby the operator can continually observe the state of the cannula.

Additionally, the entire probe can be removed easily from around the cannula without disturbing the position of the cannula, for any purpose such as the taking of X-ray exposures. With the aid of the corrugated faces 24, 25, the adapter can be slid upwardly enough to disengage the projections 30 and removed forwardly from the probe. The carrier of the probe can then be slid along the body of the patient in the opposite direction, leaving the cannula undisturbed.

The formation of the guide path or paths between the channels of the adapter and the lateral inner wall of the carrier greatly facilitates the complete removal of the probe from around the emplaced cannula.

It is to be understood that the shape of the cannula guide adapter may be modified without departing from the scope or spirit of this invention.

What is claimed is:

1. An ultrasonic transducer probe for use in inserting a cannula through a region of a subject to be examined comprising:
    a block-like carrier with a plurality of ultrasonic transducer elements arranged along an application surface of said carrier adapted to be positioned on the body surface of the subject, and including a wedge-shaped cavity extending from a relatively large area in the surface opposite said application surface to a slot opening in the application surface, the inner vertical boundary of said cavity being the inner lateral wall of the carrier, and
    a wedge-shaped cannula guide adapter complementary in shape to said cavity and dimensioned to removably and securely fit within said cavity of the carrier, said adapter having channel means in a lateral surface thereof for forming at least one cannula guide path in combination with said lateral wall when said adapter is inserted into said cavity, said guide path extending from the wide surface to the narrow end of said adapter and being aligned with said slot.

2. The ultrasonic transducer probe of claim 1 wherein said channel means is a shallow triangular cavity having its wide end in the wide surface of said wedge-shaped adapter.

3. The ultrasonic transducer probe of claim 1 wherein said channel means includes a plurality of channels radiating away from said slot when said adapter is inserted into said carrier.

4. The ultrasonic transducer probe of claim 1 wherein said channel means comprise a single channel forming a single guide path perpendicular to said application surface when said adapter is fitted in said carrier.

5. An ultrasonic transducer probe for use in inserting a cannula through a region of a subject to be examined comprising:
    a block-like carrier with a plurality of ultrasonic transducer elements arranged along an application surface of said carrier adapted to be positioned on the body surface of the subject, and including a wedge-shaped cavity extending from a relatively large area in the surface opposite said application surface to a slot opening in the application surface, the inner vertical boundary of said cavity being the inner lateral wall of the carrier, and
    a wedge-shaped cannula guide adapter complementary in shape to said cavity and dimensioned to removably and securely fit within said cavity of the carrier, said adapter having channel means in a lateral surface thereof for forming at least one cannula guide path in combination with said lateral wall when said adapter is inserted into said cavity, said guide path extending from the wide surface to the narrow end of said adapter and being aligned with said slot, wherein said cannula guide adapter is reversible, either of the lateral surfaces of the adapter being selectably positionable facing said inner lateral wall of said carrier and wherein channel means are provided on the opposite lateral surfaces of said adapter.

6. The ultrasonic transducer probe of claim 5 wherein the sides of said wedge-shaped cavity are formed by two opposing pairs of tapering surfaces, the tapering surfaces of the pairs on each side of the cavity being offset by surfaces parallel to said application surface, the outer side surfaces of said adapter being complementary to said tapering surfaces and said offsetting surface.

7. The ultrasonic transducer probe of claim 6 also including projections extending outwardly from said pair of tapering surfaces diverging outwardly from said offsetting surfaces and wherein the surface of said adapter complementary to said diverging surfaces includes grooves for receiving said projections.

8. The ultrasonic transducer probe of claim 7 wherein the wide surface of said wedge-shaped adapter is parallel to but positioned below the surface of said carrier opposite said application surface, when said adapter is fitted into said carrier.

9. The ultrasonic transducer probe of claim 8 wherein the wide surface of said adapter is positioned approximately half way between said offsetting surfaces and said surface of said carrier opposite said application surface when said adapter is fitted into said carrier.

10. The ultrasonic transducer probe of claim 9 wherein said projections extend a relatively short distance toward said surface of said carrier opposite said application surface for permitting said adapter to be moved away from said projections perpendicularly to said offsetting surfaces and then vertically from said lateral wall of said carrier without moving the wide surface of the adapter up to the surface of the carrier opposite said application surface.

11. The ultrasonic transducer probe of claim 10, wherein the inner and outer lateral surfaces of the portions of said adapter lying between said offsetting surfaces and said wide surface of said adapter, when said adapter is fitted into said carrier, are corrugated to facilitate handling of the adapter.

* * * * *